United States Patent [19]
Ranken et al.

[11] 3,971,634
[45] July 27, 1976

[54] HEAT PIPE METHANATOR

[75] Inventors: William A. Ranken; Joseph E. Kemme, both of Los Alamos, N. Mex.

[73] Assignee: The United States of America as represented by the United States Energy Research and Development Administration, Washington, D.C.

[22] Filed: Apr. 25, 1975

[21] Appl. No.: 571,655

[52] U.S. Cl. .............................. 48/120; 23/288 M; 165/105; 260/449 M
[51] Int. Cl.² .......................................... C10B 1/00
[58] Field of Search .......... 23/288 M, 288 K, 288 L; 48/119, 120; 165/105; 260/449 M

[56] References Cited
UNITED STATES PATENTS

| | | | |
|---|---|---|---|
| 2,778,610 | 1/1957 | Bruegger | 23/288 R |
| 3,734,173 | 5/1973 | Moritz | 165/105 |
| 3,779,310 | 12/1973 | Russell | 165/105 |

*Primary Examiner*—Robert L. Lindsay, Jr.
*Assistant Examiner*—George C. Yeung
*Attorney, Agent, or Firm*—Dean E. Carlson; Jerome B. Rockwood

[57] ABSTRACT

A heat pipe methanator for converting coal gas to methane. Gravity return heat pipes are employed to remove the heat of reaction from the methanation promoting catalyst, transmitting a portion of this heat to an incoming gas pre-heat section and delivering the remainder to a steam generating heat exchanger.

12 Claims, 6 Drawing Figures

HEAT PIPE METHANATOR

BACKGROUND OF THE INVENTION

When making a synthetic natural gas from coal, the raw product gas must be upgraded to a high BTU pipeline quality gas. This is done by using the shift reaction to increase the hydrogen-carbon dioxide ratio in the raw gas. This mixture is then passed through a catalyst bed where it reacts exothermally to give a nominal yield of $CH_4 + H_2O$.

A major problem in the design of methanator units is removal of heat from the catalyst. If the catalyst temperature is not held within relatively narrow limits the poisoning rate increases sharply and catalyst lifetime is reduced. An even more serious consequence of inadequate removal is the formation of hot spots, which can propagate and rapidly destroy the effectiveness of a catalyst.

One method heretofore employed for cooling methanator catalyst beds is to employ the heat capacity of the reacting mixture to remove the reaction heat. The gas is recycled through a methanator with heat removed in an external loop. Another approach in the prior art is to place the catalyst in pellet form in tubes that are surrounded by a heat transfer fluid. The reacting gas mixture flows through the tubes and by conduction and convection transfers the heat from the catalyst pellets to the tube wall and thence to the cooling liquid. In this approach an exceptionally large number of tubes is required for cooling since cooling is insufficient if the tube diameter exceeds about 12 mm.

A third cooling method employed in the prior art consists of vertical reentrant tubes, the exterior coated with a flame sprayed nickel catalyst. Heat generated by the reacting gas mixture flowing along an array of such tubes is removed by boiling heat exchange fluid. The heat exchange fluid is introduced into each reentrant tube by gravity flow through the inner tube of the concentric pair and flows up the annulus between the two tubes. Temperature is controlled by using an inert gas overpressure to control the boiling point. Since catalyst changes are required two or three times a year, each of the reentrant tubes would have to be removable so that the depleted catalyst could be taken off and replaced. This requires the use of many relatively large high pressure flanges which are difficult to put in the available space and are subject to leakage. A modification of this design to eliminate the necessity of the flanges is similar to the tube-in-vat approach described hereinabove except that the catalyst is applied by flame-spraying the inner wall of the tubes. In this approach catalyst removal and reapplication can be done in place. The tubes can be permanently welded to the end plates of the methanator. However, flame-spraying the catalyst on the inner wall of the tube requires an excessive amount of time since application rates are approximately 1 foot per hour and tube lengths are approximately 30 feet. It will be apparent that replacing the catalyst in a practical methanator containing as many as 1200 tubes is a time consuming operation.

SUMMARY OF THE INVENTION

The present invention takes advantage of the self-contained heat transfer capability of the heat pipe to provide a methanator with a simple configuration combining the catalyst bed incoming gas preheat section and thermal recovery in one unit. The catalyst is sprayed on the outer wall of each easily removable heat pipe, enabling easy replaceability of the catalyst.

DETAILED DESCRIPTION

Figure 1:
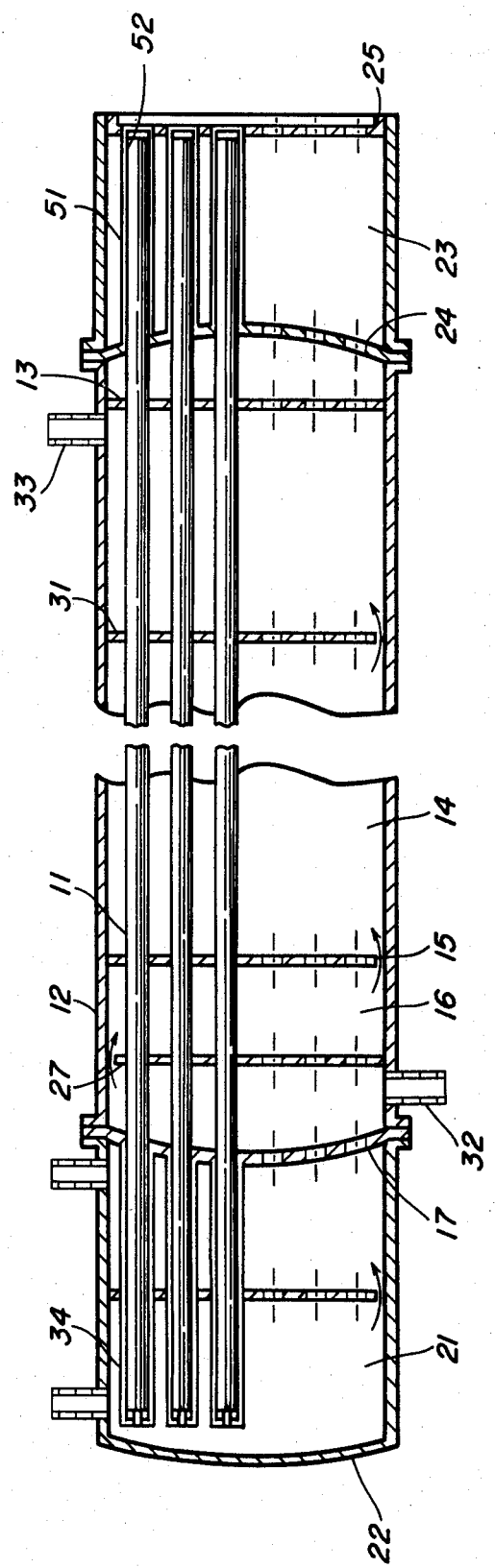
FIG. 1 is a cross sectional drawing schematically illustrating the heat pipe methanator of the present invention.

Referring now to FIG. 1, an array of gravity return heat pipes 11 are enclosed in a pressure shell 12. Heat pipes 11 are supported by a grid plate 13. The pressure shell 12 encloses a methanation section 14 extending from baffle 15 to grid plate 13. A preheat section 16 extends from the high pressure bulkhead 17 to baffle 15. Heat exchanger section 21 extends from bulkhead 17 to end of bulkhead 22. A start-up heat exchanger 23 may be provided at the other end of the pressure vessel 12. Start-up heat exchanger 23 is defined by a bulkhead 24 and plate 25. Additional flow baffles 27, 31 and others not shown are provided to lengthen the gas flow path between inlet 32 and outlet 33. In the methanation section incoming gas through inlet 32, including hydrogen and carbon monoxide, passes through the preheat section 16, reaching the temperature of about 650°K. This temperature is required for the methanation reaction to take place at the desired rate. The gas is then passed into the methanating section 14. In the preheat section the heat pipes are roughened to facilitate heat transfer and in the methanation section the heat pipes are coated with a catalyst.

In operation heat is generated by the methanation reaction along the catalyst coated section of the heat pipes. This section is approximately two-thirds of the total heat pipe length due to the limitation of heat input by the reaction rate. The reaction heat vaporizes the working fluid of the heat pipe and is transmitted by vapor flow toward the heat exchanger 21. Approximately one-fourth of the total heat is deposited by the vapor condensation in the preheat section 16 bringing the incoming gas up to temperature. The remainder is delivered to the heat exchanger 21. In each heat pipe the condensed vapor is returned by gravity flow to the catalyst coated section of the pipe. Heat transfer in the heat exchanger occurs by conduction through annular gas gaps between the heat pipes 11 and the interior walls of the thimbles 34. The sizing of the gap depends on the temperature desired in the heat exchanger, as well as the steady state composition of the gas mixture in the gap and the length of the heat exchanger thimble 34. In addition, this gap enables easy insertion of the heat pipes.

Figure 3:
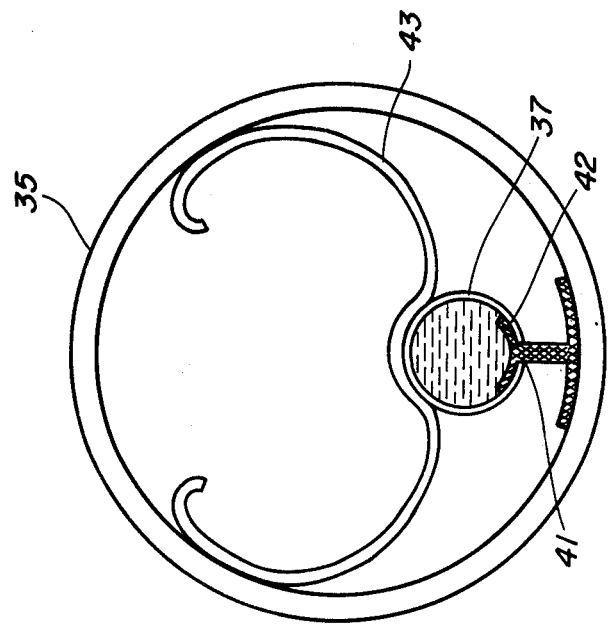
FIG. 3 is a cross section illustrating the reaction chamber section of a heat pipe.
Figure 2:
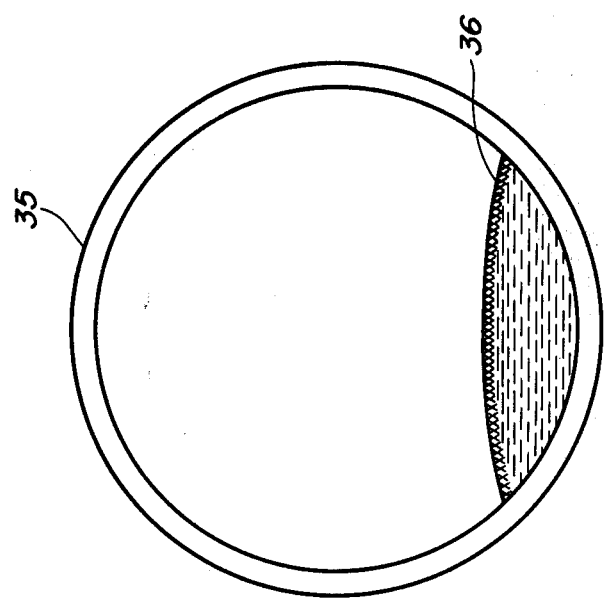
FIG. 2 is a cross section showing the heat exchanger section of a heat pipe.

Since the heat pipes are tilted about 4° the force of gravity returns the condensed working fluid to the evaporator section of the heat pipe. Since the return flow is inhibited by the interaction with vapor flowing in the opposite direction, baffle channels are provided for this return flow. FIG. 2 illustrates in cross section the heat pipe in the condenser section 21. FIG. 3 illustrates a cross section of the heat pipe in the evaporator section 14. In the condenser section vapor condensing on the inside of the tube wall 35 flows to the bottom of the tube and proceeds along the bottom by gravity to a transition region where it is diverted into the artery cross section configuration illustrated in FIG. 3. A baffle 36 of screening is placed at the bottom of the tube in the condenser section to reduce the vapor liquid counter flow interaction and yet not interfere with the circumferential flow of condensed liquid to the bottom of the tube.

The artery in the evaporator section of the heat pipe is a solid wall tube 37 having a slot 41 in the bottom where several layers of fine mesh screen 42 are crimped. The wall of tube 37 shields the liquid returning from the condenser from direct interaction with the oppositely moving vapor stream. The screen mesh 42 serves to dispense the returning liquid to the evaporator tube wall capillary structure and also helps to minimize heat flow from the tube wall to the artery. The artery is retained in the heat pipe by a plurality of spring clips 43. The screen mesh 42 and the spring clips 43 provide thermal isolation of the liquid in the artery from the outer wall 35 of the heat pipe. Such isolation is required to restrict the formation of vapor in the artery and prevent appreciable vapor flow in the artery since such vapor flow would restrict the return liquid flow.

Figure 4:
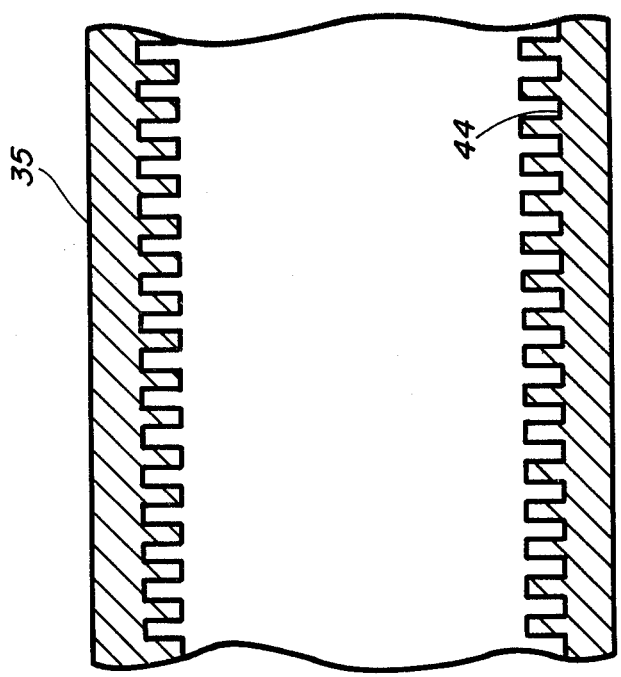
FIG. 4 is a longitudinal section showing one method of distributing the working fluid about the circumference of the heat pipe.

The liquid from artery 37 is applied to the inner wall of tube 35 by screened dispenser 42. The liquid is carried around the circumference of the inner wall of the heat pipe by a wicking action. In one embodiment illustrated in FIG. 4, the wicking action is provided by a multiplicity of grooves 44 circumferentially cut into the inner wall of the heat pipe. These grooves distribute liquid from the artery to the entire inside surface of the heat pipe. In the condenser section, the grooves serve to increase the effective heat transfer area. Capillary forces tend to draw the condensate to the bottom of the grooves and to prevent the build-up of a low conductivity film on the entire condenser surface.

Figure 5:
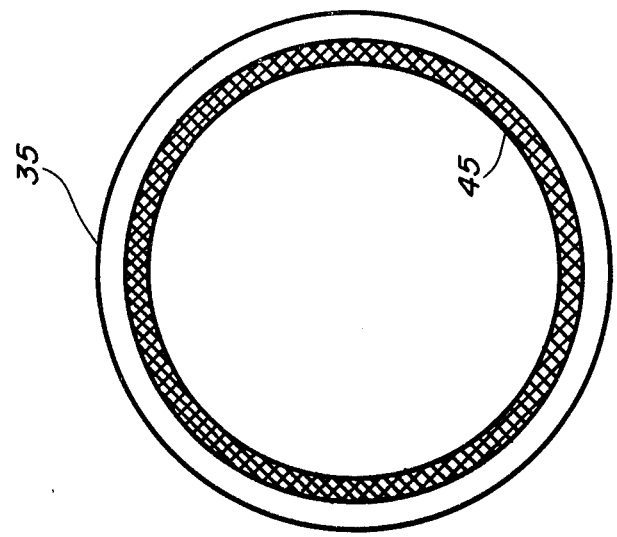
FIG. 5 is a cross sectional view of a heat pipe illustrating an alternate method of distributing the working fluid about the circumference of the pipe.

An alternative method of circumferentially distributing the liquid in the evaporator is illustrated in FIG. 5. In this approach the inner wall of the heat pipe is lined with one or two layers of screen.

Figure 6:
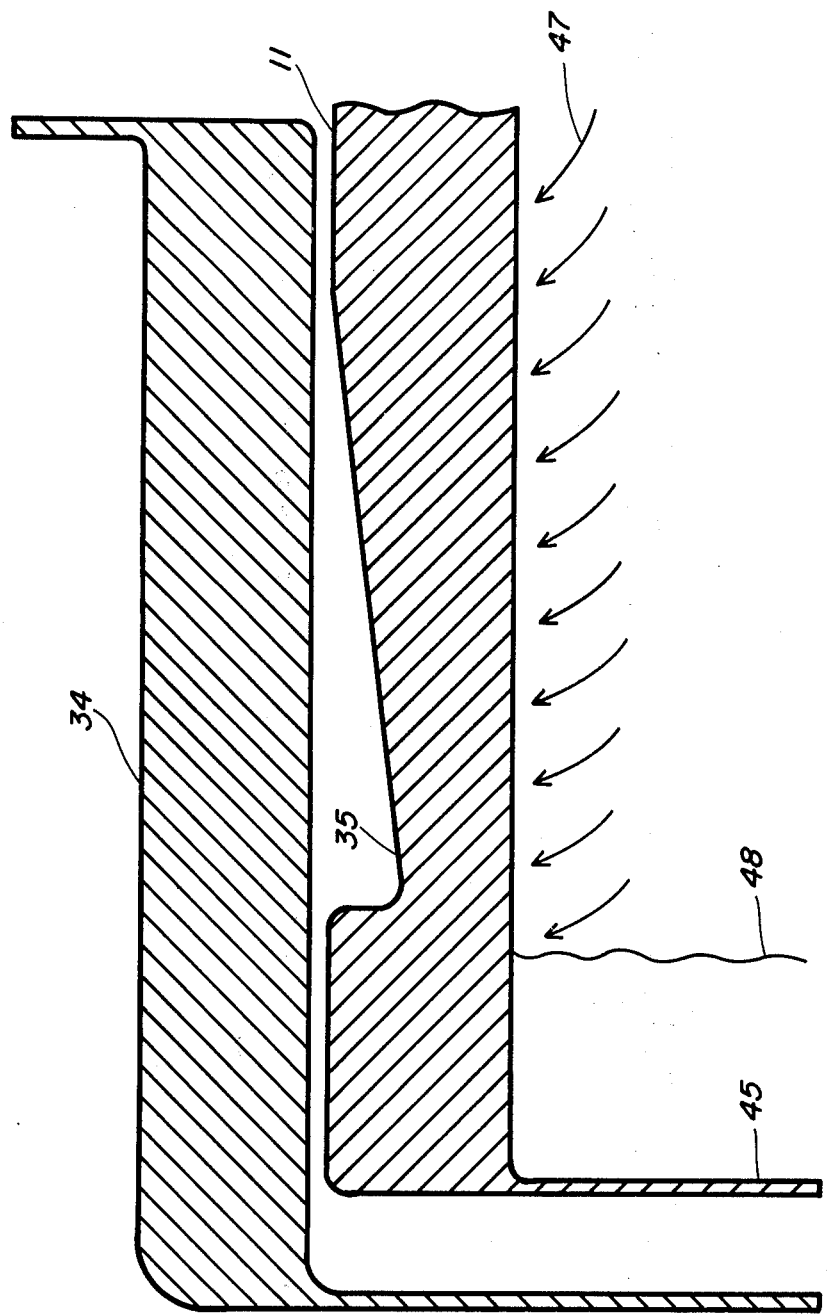
FIG. 6 illustrates the construction of the heat exchanger end of a heat pipe.

Temperature control of the heat pipe 11 is accomplished by adding an inert gas and providing a region at the condenser end of the heat pipe where the heat deposition rate increases rapidly with axial distance, illustrated in FIG. 6. The working fluid vapor, indicated by arrows 47, pumps the inert gas to the vicinity of the condenser end wall 45 of the heat pipe, where a vapor inert gas interface 48 is established. Volume occupied by the inert gas decreases or increases as the input heat increases or decreases respectively, with more or less heat transfer area being required to dump the heat transmitted to the heat exchanger. Volume changes result in inverse changes of pressure, establising the vapor pressure of the working fluid and therefore its operating temperature. Since the vapor temperature of the fluid generally increases rapidly with temperature, relatively large pressure variation can occur without causing undue change in operating temperature. The temperature can be varied by changing the quantity of inert gas added to the heat pipe. In addition, the configuration of the wall 35, in connection with the position of the interface 48 determines the heat removal characteristic for establishing temperature control.

The gas gap established by the profile of wall 35 provides control for thermal coupling between the individual heat pipes and the interior thimble walls 34 of the heat exchanger end plate. This design also does away with the requirement for high pressure feedthroughs for individual tubes. The gap size and profile depends on the desired change in temperature, the length and diameter of the thimble 34 and the amount of heat flow transmitted from the heat pipe. In addition the gap size depends upon the conductivity of the gas in the gap. As is apparent from FIG. 1 the gas in the gap is essentially the gas in the preheat section 16 of the reaction chamber.

The gas gap is tapered since the water temperature in the heat exchanger increases by about 300°K as it flows from the region at the ends of the heat pipes toward the end plate 17. The configuration of the gap is also determined by the effect of axial variations in vapor condensation rate on the performance of the heat pipe and the desired change in heat transfer rate.

The section 23 of the methanator as illustrated in FIG. 1 is provided to enable start-up of the reaction. For the methanation reaction to be initiated the incoming gas must be heated to about 640°K. During operation this is accomplished in the pre-heat section 16 as disclosed hereinabove. One method of applying start-up heat in start-up section 23 is to provide plurality of electrical strip heaters 51 about the walls of thimbles 52 into which the heat pipes are fitted in a manner similar to thimbles 34. Alternatively a gas burner may be employed to feed hot gases through pre-heat section 23. These heat sources may be used to heat the heat pipes directly and in turn heat the incoming charge of gas contained in the methanator unit. During start-up the gas in the methanator is initially hydrogen to which carbon monoxide is added when the self-operating temperature of a catalyst is reached.

A number of working fluids may be employed in the heat pipes. As is apparent, the working fluid must have a significant vapor pressure in the methanation reaction range of approximately 640° to 760°K. Mercury, cesium, potassium, and sulfur may be employed. In addition, a variety of high molecular weight organic materials are known.

It is to be understood that the invention is not limited to the specific features and embodiments hereinabove set forth, but may be carried out in other ways without departing from the spirit and scope of the invention as defined by the following claims.

What we claim is:

1. A coal gas methanator of the type employing heat pipes comprising:

an elongated pressure shell having a methanation section, a preheat section, a heat exchanger section and a start-up heat exchanger section;

separating means for separating said heat exchanger section from said methanation section and for separating said start-up heat exchanger section from said methanation section;

a plurality of heat pipes enclosed in said elongated pressure shell;

heat pipe supporting means in said separating means;

A catalyst coating on the exterior walls of said plurality of heat pipes in said methanation section, said catalyst reacting hydrogen and carbon monoxide to produce methane in an exothermic reaction;

transfer means containing a working fluid within said plurality of heat pipes to transfer the heat of reaction at constant temperature from said methanation section to said preheat section, and to transfer remaining heat to said heat exchanger section; and temperature control means including an inert gas in said plurality of heat pipes together with said working fluid to vary the amount of working fluid in the heat exchanger section, keeping the temperature in said methanation section constant.

2. In the coal gas methanator set forth in claim 1, said transfer means comprising:

means enabling evaporation of said working fluid in said heat pipes in the region of said methanation section and conducting said evaporated working fluid to said preheat section.

3. In the coal gas methanator set forth in claim 2, said heat exchanger section condensing said evaporated working fluid.

4. In the coal gas methanator set forth in claim 3, means for returning said working fluid in liquid form to said methanation section.

5. In the coal gas methanator set forth in claim 4, said means for returning said working fluid comprising:

separating means for separating liquid working fluid from gaseous working fluid; and providing a tilt in said heat pipes enabling said liquid working fluid to return to the methanation section.

6. In the coal gas methanator set forth in claim 5, said separating means comprising:

perforated baffle means in the heat exchanger section of said heat pipe enabling condensed working fluid to flow beneath said baffle means;

an artery in the methanation section of said heat pipes to return said working fluid condensed under said baffle to said methanation section; and, dispensing means for dispersing said condensed working fluid from said artery to the inner walls of the heat pipes in the methanation section.

7. In the coal gas methanator set forth in claim 6, said dispensing means comprising:

an aperture in said artery;

wick means on the inner walls of said heat pipe; and dispensing means connecting said aperture to said wick means.

8. In the coal gas methanator set forth in claim 7, said wick means comprising screening lining the inner wall of the heat pipe.

9. In the coal gas methanator set forth in claim 7, said wick means comprising a plurality of circumferential grooves in the inner wall of the heat pipe.

10. In a heat pipe methanator, the combination of:

a reaction chamber and a heat exchanger;

a heat pipe having an evaporating section in operative relation with said reaction chamber and a condensing section in operative relation with said heat exchanger;

thimble means in said heat exchanger for receiving said condensing section;

means for containing a working fluid in said heat pipe; and temperature control means including an inert gas in said heat pipe, held by said working fluid adjacent the end wall of said condensing section.

11. In the heat pipe methanator set forth in claim 10, said thimble means having a first end open to said reaction chamber and adapted to receive the condensing end of said heat pipe, and a closed end sealing said reaction chamber from said heat exchanger.

12. In the heat pipe methanator set forth in claim 11, said temperature control means including a varying reduced wall thickness on said heat pipe in said condensing section defining a varying width gap between the inner wall of said thimble and the outer wall of said heat pipe, and enabling expansion and contraction of said inert gas to control the amount of heat supplied by said working fluid to said heat exchanger.

* * * * *